United States Patent
Jansen et al.

(10) Patent No.: US 10,092,315 B2
(45) Date of Patent: Oct. 9, 2018

(54) PENETRATING MEMBER WITH DIRECT VISUALIZATION

(75) Inventors: Lex P. Jansen, Pleasanton, CA (US);
Singfatt Chin, Pleasanton, CA (US);
John T. To, Newark, CA (US)

(73) Assignee: Expanding Innovations, Inc., Mountain View, CA (US)

( * ) Notice: Subject to any disclaimer, the term of this patent is extended or adjusted under 35 U.S.C. 154(b) by 445 days.

(21) Appl. No.: 12/510,145

(22) Filed: Jul. 27, 2009

(65) Prior Publication Data

US 2010/0191057 A1    Jul. 29, 2010

Related U.S. Application Data

(60) Provisional application No. 61/084,202, filed on Jul. 28, 2008.

(51) Int. Cl.
*A61B 1/00* (2006.01)
*A61B 17/34* (2006.01)
(Continued)

(52) U.S. Cl.
CPC ........ *A61B 17/3401* (2013.01); *A61B 1/0051* (2013.01); *A61B 1/00082* (2013.01);
(Continued)

(58) Field of Classification Search
CPC ....... A61B 1/00101; A61B 1/05; A61B 1/018; A61B 1/00096; A61B 1/00082; A61B 1/0051; A61B 1/3137; A61B 1/0008; A61B 1/00087; A61B 1/00089; A61B 1/00135; A61B 1/00137; A61B 1/00142; A61B 1/042

USPC ....... 600/127, 118, 249, 109, 106, 135, 142, 600/156, 141, 245, 190, 104, 129, 175, 600/176, 114, 115, 121–125, 167;
(Continued)

(56) References Cited

U.S. PATENT DOCUMENTS 2,932,294 A * 4/1960 Fourestier et al. ........... 600/177
3,941,121 A * 3/1976 Olinger et al. ............... 600/167
(Continued)

OTHER PUBLICATIONS

International Search Report dated Nov. 24, 2009, for PCT Patent Application No. PCT/US2009/051883, filed on Jul. 27, 2009, 6 pages.
(Continued)

*Primary Examiner* — Timothy J Neal
*Assistant Examiner* — Aaron B Fairchild
(74) *Attorney, Agent, or Firm* — Morrison & Foerster LLP; Ross M. Carothers

(57) ABSTRACT

Systems and methods for accessing the spine include tissue penetrating members with direct visualization capability that may be used to form an access pathway to a targeted treatment site. The direct visualization capability, which may be provided by fiberoptic illumination and imaging components, may be use to visualize the tissue as the access pathway is formed by the tissue penetrating member. The tissue penetrating members include catheters and cannulas with sharpened tips with integrated fiberoptic components and/or channels in which a fiberscope or miniscope may be inserted. Apertures and/or transparent materials are provided to permit imaging of tissue about the distal end of the tissue penetrating member.

15 Claims, 14 Drawing Sheets

(51) Int. Cl.
*A61B 1/313* (2006.01)
*A61B 1/005* (2006.01)
*A61B 17/32* (2006.01)
*A61B 17/3211* (2006.01)
*A61B 90/00* (2016.01)

(52) U.S. Cl.
CPC ...... *A61B 1/00087* (2013.01); *A61B 1/00096* (2013.01); *A61B 1/3135* (2013.01); *A61B 1/3137* (2013.01); *A61B 17/3211* (2013.01); *A61B 17/320016* (2013.01); *A61B 17/3478* (2013.01); *A61B 90/361* (2016.02); *A61B 2017/3454* (2013.01)

(58) Field of Classification Search
USPC ...... 606/206, 185, 144, 33, 167; 604/70, 26, 604/43, 21, 27, 214, 517
See application file for complete search history.

(56) References Cited

U.S. PATENT DOCUMENTS

| | | | |
|---|---|---|---|
| 4,403,956 A | | 9/1983 | Nakanishi |
| 4,423,436 A | * | 12/1983 | Kimura ................. A61B 1/042 348/69 |
| 4,736,733 A | * | 4/1988 | Adair ..................... A61B 1/042 600/109 |
| 4,807,597 A | | 2/1989 | Tsuno et al. |
| 4,899,732 A | | 2/1990 | Cohen |
| 5,159,920 A | * | 11/1992 | Condon et al. ................ 600/129 |
| 5,329,935 A | * | 7/1994 | Takahashi .......... A61B 1/00142 600/121 |
| 5,483,951 A | * | 1/1996 | Frassica ............. A61B 1/00142 600/104 |
| 5,573,493 A | * | 11/1996 | Sauer ................. A61B 1/00101 600/121 |
| 5,741,261 A | | 4/1998 | Moskovitz et al. |
| 5,762,604 A | * | 6/1998 | Kieturakis ................... 600/115 |
| 5,797,944 A | * | 8/1998 | Nobles et al. ............... 606/185 |
| 5,871,470 A | * | 2/1999 | McWha ....................... 604/158 |
| 6,007,483 A | * | 12/1999 | Kieturakis .................. 600/115 |
| 6,264,668 B1 | * | 7/2001 | Prywes ........................ 606/167 |
| 6,447,444 B1 | * | 9/2002 | Avni ..................... A61B 1/0005 600/109 |
| 6,544,214 B1 | | 4/2003 | Utterberg |
| 6,564,087 B1 | * | 5/2003 | Pitris et al. .................. 600/478 |
| 6,902,547 B2 | * | 6/2005 | Ayes et al. ................... 604/272 |
| 7,534,243 B1 | * | 5/2009 | Chin ................ A61B 17/00008 606/41 |
| 7,766,878 B2 | * | 8/2010 | Tremaglio et al. ....... 604/167.05 |
| 7,952,718 B2 | * | 5/2011 | Li et al. ........................ 356/479 |
| 8,050,523 B2 | * | 11/2011 | Younge et al. .................. 385/13 |
| 8,128,590 B2 | * | 3/2012 | Albrecht et al. ................ 604/23 |
| 8,277,411 B2 | * | 10/2012 | Gellman ....................... 604/131 |
| 8,343,035 B2 | * | 1/2013 | To ................................. 600/109 |
| 2001/0004676 A1 | | 6/2001 | Ouchi ........................... 600/106 |
| 2001/0056278 A1 | * | 12/2001 | Nield et al. ..................... 606/15 |
| 2002/0007144 A1 | * | 1/2002 | Snoke ........................ 604/95.04 |
| 2002/0198456 A1 | * | 12/2002 | Snoke ........................... 600/464 |
| 2003/0004460 A1 | * | 1/2003 | Bedell ....................... 604/95.04 |
| 2003/0028147 A1 | * | 2/2003 | Ayes et al. .................. 604/164.06 |
| 2003/0144594 A1 | * | 7/2003 | Gellman ....................... 600/466 |
| 2003/0149400 A1 | * | 8/2003 | Banik et al. ............. 604/103.01 |
| 2003/0181905 A1 | * | 9/2003 | Long .............................. 606/46 |
| 2003/0225402 A1 | * | 12/2003 | Stevens et al. ................. 606/39 |
| 2004/0158125 A1 | * | 8/2004 | Aznoian et al. .............. 600/106 |
| 2005/0065543 A1 | * | 3/2005 | Kahle et al. .................. 606/190 |
| 2005/0283048 A1 | * | 12/2005 | Gill et al. ....................... 600/121 |
| 2005/0288622 A1 | * | 12/2005 | Albrecht et al. ................ 604/23 |
| 2006/0173479 A1 | * | 8/2006 | Smith ........................... 606/185 |
| 2007/0076429 A1 | * | 4/2007 | Ohkubo ......................... 362/572 |
| 2007/0083081 A1 | * | 4/2007 | Schlagenhauf et al. ...... 600/104 |
| 2007/0122462 A1 | | 5/2007 | Chandra et al. |
| 2007/0167681 A1 | * | 7/2007 | Gill et al. ....................... 600/112 |
| 2007/0167736 A1 | * | 7/2007 | Dietz et al. .................... 600/411 |
| 2007/0167978 A1 | * | 7/2007 | Yamamoto et al. .......... 606/205 |
| 2007/0197864 A1 | * | 8/2007 | Dejima et al. ............... 600/106 |
| 2007/0260273 A1 | * | 11/2007 | Cropper et al. .............. 606/185 |
| 2008/0064925 A1 | * | 3/2008 | Gill et al. ....................... 600/109 |
| 2008/0287961 A1 | * | 11/2008 | Miyamoto et al. ........... 606/127 |
| 2009/0062871 A1 | * | 3/2009 | Chin et al. ................... 606/86 R |
| 2009/0062872 A1 | * | 3/2009 | Chin et al. ................... 606/86 R |
| 2009/0253967 A1 | * | 10/2009 | Gill et al. ....................... 600/249 |

OTHER PUBLICATIONS

Written Opinion of the International Searching Authority dated Nov. 24, 2009, for PCT Patent Application No. PCT/US2009/051883, filed on Jul. 27, 2009, 6 pages.

* cited by examiner

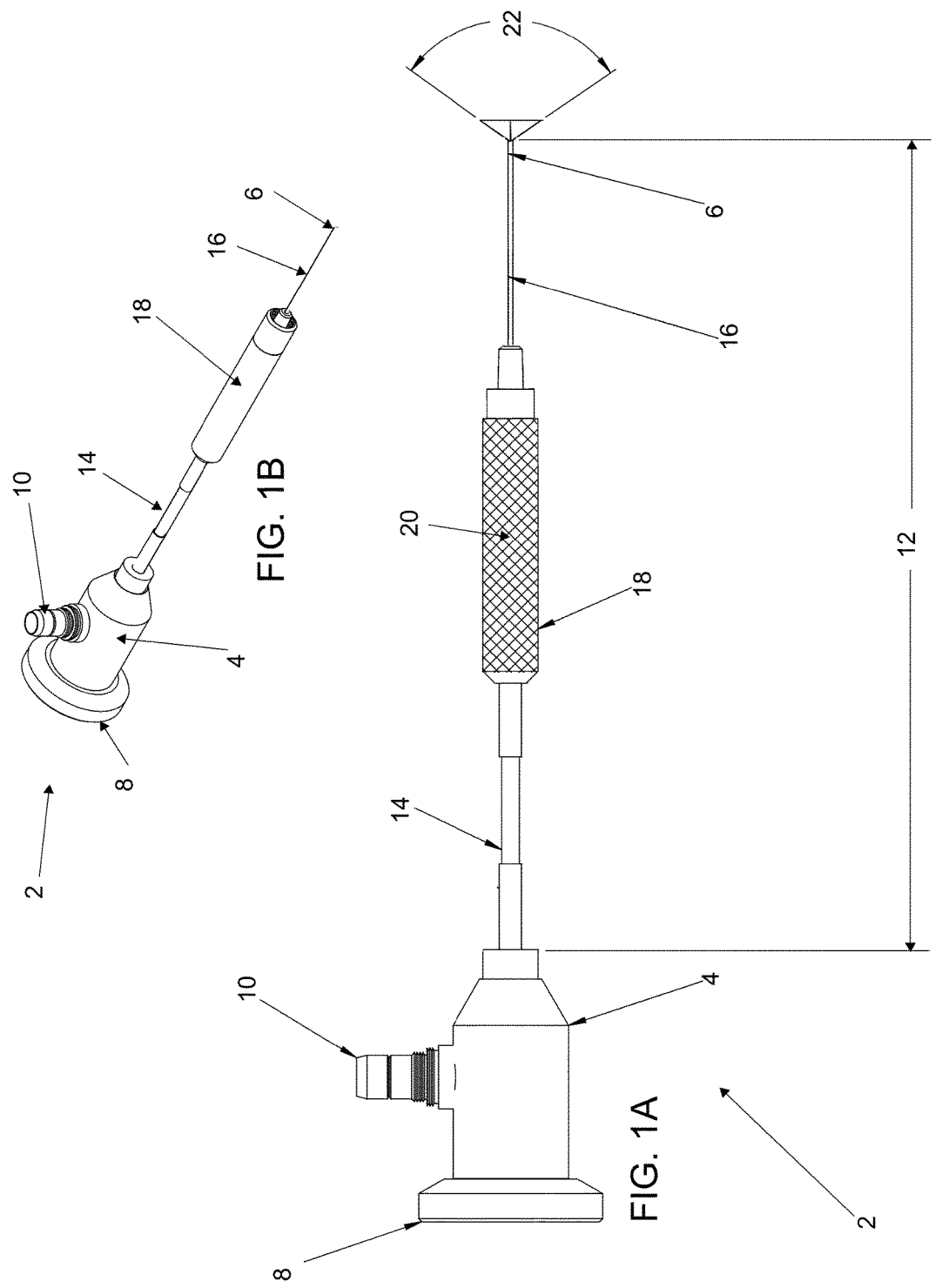

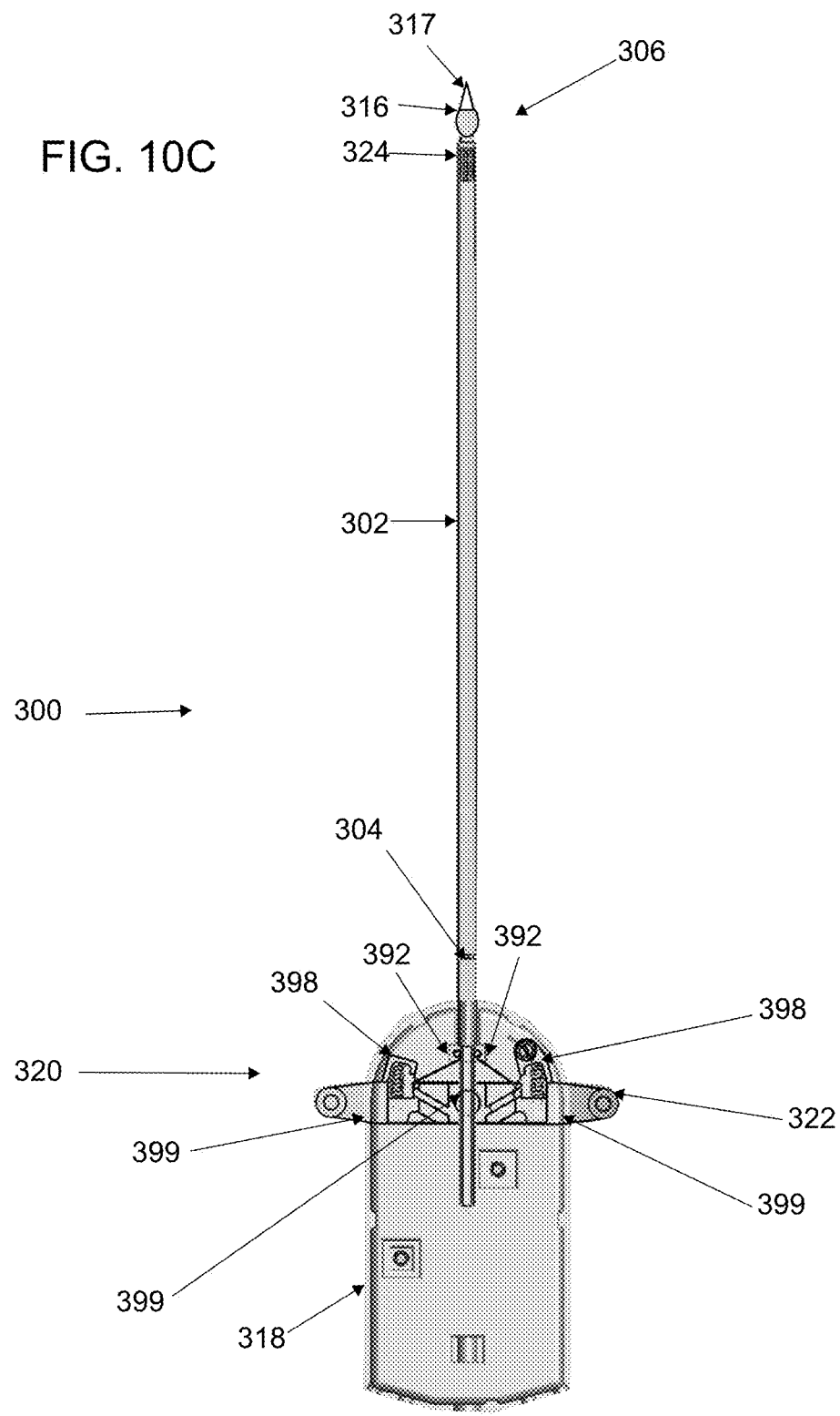

PENETRATING MEMBER WITH DIRECT VISUALIZATION

CROSS-REFERENCE TO RELATED APPLICATIONS

The present application claims priority under 35 U.S.C. § 119(e) to U.S. Provisional Application No. 61/084,202 filed on Jul. 28, 2008, the disclosure of which is hereby incorporated by reference in their entirety.

BACKGROUND OF THE INVENTION

Injured intervertebral discs are generally treated with bed rest, physical therapy, modified activities, and pain medications for substantial treatment durations. There are also a number of treatments that attempt to repair injured intervertebral discs and to avoid surgical removal of injured discs. For example, disc decompression is a procedure used to remove or shrink the nucleus, thereby decompressing and decreasing the pressure on the annulus and nerves. Less invasive procedures, such as microlumbar discectomy and automated percutaneous lumbar discectomy, remove the nucleus pulposus of a vertebral disc by aspiration through a needle laterally inserted into the annulus. Another procedure involves implanting a disc augmentation device in order to treat, delay, or prevent disc degeneration. Augmentation refers to both (1) annulus augmentation, which includes repair of a herniated disc, support of a damaged annulus, and closure of an annular tear, and (2) nucleus augmentation, which includes adding material to the nucleus. Many conventional treatment devices and techniques, including open surgical approaches, involve muscle dissection or percutaneous procedures to pierce a portion of the disc under fluoroscopic guidance, but without direct visualization. Several treatments also attempt to reduce discogenic pain by injecting medicaments or by lysing adhesions in the suspected injury area. However, these devices also provide little in the form of tactile sensation for the surgeon or allow the surgeon to atraumatically manipulate surrounding tissue. In general, these conventional systems rely on external visualization for the approach to the disc and thus lack any sort of real time, on-board visualization capabilities.

Medication and physical therapy may be considered temporary solutions for spine-related disorders. These therapies, however, may not fully address the underlying pathologies. In contrast, current surgical solutions such as laminectomy, where the laminae (thin bony plates covering the spinal canal) are removed, permit exposure and access to the nerve root which does address the underlying pathologies. From there, bone fragments impinging the nerves may be removed. Screws, interbody spacers, and fixation plates may also be used to fuse or stabilize the spine following laminectomy. These surgical techniques, however, are highly invasive and often require extensive muscle dissection to achieve adequate surgical exposure, which results in prolonged surgical duration under general anesthesia and extended recovery periods. Bone tissue is sometimes removed to improve surgical access, but may also increase the risk of injury to nearby neurovascular structures. Other surgical methods have been attempted, such as laminotomy, which focuses on removing only certain portions or smaller segments of the laminae.

Furthermore, accurately diagnosing back pain is often more challenging than many people expect and may involve a combination of a thorough patient history and physical examination, as well as a battery of diagnostic tests. A major problem is the complexity of the various components of the spine as well as the broad range of physical symptoms experienced by individual patients. In addition, the epidural space contains various elements such as fat, connective tissue, lymphatics, arteries, veins, blood, and spinal nerve roots. These anatomical structures make it difficult to treat or diagnose conditions within the epidural area because they tend to collapse around any instrument or device inserted therein. This may reduce visibility in the epidural space, and may cause inadvertent damage to nerve roots during device insertion. Also, the insertion of a visualization device may result in blocked or reduced viewing capabilities. As such, many anatomical elements within the epidural space may limit the insertion, movement, and viewing capabilities of any access, visualization, diagnostic, or therapeutic device inserted into the epidural space.

BRIEF SUMMARY OF THE INVENTION

Systems and methods for accessing the spine include tissue penetrating members with direct visualization capability that may be used to form an access pathway to a targeted treatment site. The direct visualization capability, which may be provided by fiberoptic illumination and imaging components, may be use to visualize the tissue as the access pathway is formed by the tissue penetrating member. The tissue penetrating members include trocars, catheters and cannulas with sharpened tips with integrated fiberoptic components and/or channels in which a fiberscope or miniscope may be inserted. Apertures and/or transparent materials are provided to permit imaging of tissue about the distal end of the tissue penetrating member.

BRIEF DESCRIPTION OF THE DRAWINGS

The invention is best understood from the following detailed description when read in conjunction with the accompanying drawings. It is emphasized that, according to common practice, the various features of the drawings may or may not be to-scale. On the contrary, the dimensions of the various features may be arbitrarily expanded or reduced for clarity. Included in the drawings are the following figures:

FIGS. 1A and 1B are perspective and side elevational views of a fiberoptic scope;

FIG. 10C is a cut-away view of the penetrating member in FIG. 10A with a portion of the housing removed;

DETAILED DESCRIPTION OF THE INVENTION

Figure 2A:
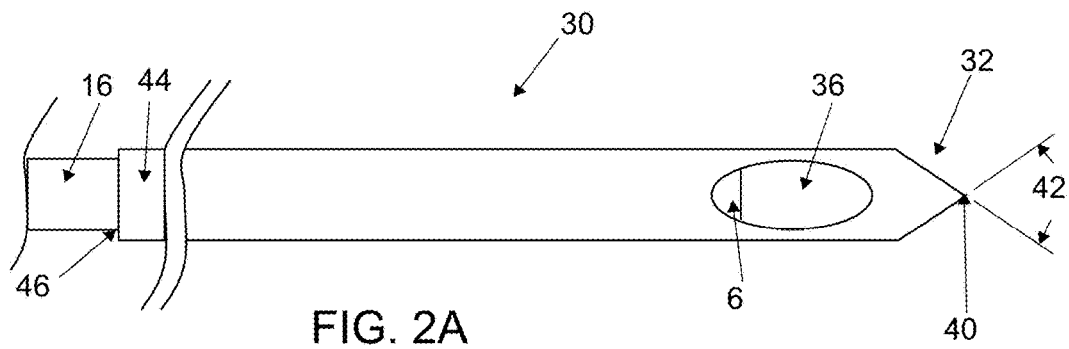
FIGS. 2A and 2B are superior and side elevational views of a tubular penetrating member with an inserted fiberoptic scope.

To reduce injury to the spine structures while preserving the strength of the bones, minimally invasive spinal procedure have been used to avoid excising native bone and/or dissection of surrounding native tissues. Existing minimally invasive spinal access procedures have been performed using both fluoroscopic guidance and endoscopic visualization. While existing spinal endoscopy systems provide direct vision capability to view the treatment area in the spine or other areas of the body once it is accessed, risks of iatrogenic injury to nerves and vessels, or difficulty localizing the target site, often persist with these systems. Similar risks and difficulties are associated with a number of other minimally invasive and limited access procedures, including but not limited to the placement of subclavian and internal jugular catheters, renal biopsies, liver biopsies, paracentesis, pleuracentesis, and femoral artery access, for example.

The source of these risks may lie with the procedures used to reach the treatment site. Before actual diagnostic or interventional treatment can begin, the treatment site needs to be accessed. This is typically performed without endoscopic visualization, using a sharp-tipped guide wire, needle or trocar under fluoroscopic or x-ray imaging. While detection of bone and other calcified structures with fluoroscopy is relatively simple, the detection of soft tissue structures with fluoroscopy remains problematic, even with the injection of contrast agent(s). Thus, during fluoroscopic procedures, soft tissue structures proximate to the treatment site, such as the nerves and blood vessels, are at significant risk of accidental injury. Excessive use of fluoroscopy and other indirect imaging systems may also subject both patients and healthcare workers to long-term risks associated with ionizing radiation.

However, by providing direct or local visualization during the initial access phase of an invasive procedure, rather than after the target site has been reached, further improvements in safety may be achieved. This may be performed, for example, by providing an instrument, such as a guidewire, cannula or trocar, with a penetrating tip and a direct visualization system to view the body tissue as the penetrating tip is cutting or piercing through intact tissue to reach the target site. The target site may be solid tissue site, such as a breast mass, the wall or lumen of a body structure, or the potential or actual space of a body cavity, for example. By visualizing body tissue while achieving access to a target site, the access instrument may be reoriented if certain structures or tissues are visualized.

FIGS. 1A and 1B depicts one embodiment of a fiberoptic scope 2 that may be inserted into a patient to optically visualize tissues and structures. The scope 2 comprises a proximal housing 4 which is used to receive the visual images from the distal end 6 of the scope 2, and to optionally transmit illumination to the distal end 6. In this particular embodiment, the proximal housing 4 comprises an eyepiece 8 that may be used to view the optical images transmitted from the distal end 6 of the scope 2, as well as a connector 10 that may be used to couple the scope 2 to a video monitor and/or an illumination system. In other examples, the scope may have only the eyepiece, only the monitor/illumination coupling, or separate couplings for the monitor and illumination. The proximal housing 4 may be connected to a shaft assembly 12, which comprises a proximal shaft segment 14, a distal shaft segment 16 and an optional handle 18. There may or may not be a visible delineation between the proximal and distal shaft segments, and in some examples, the proximal and distal shaft segments may be opposite ends of a continuous shaft body. Although the depicted shaft assembly 12 In some examples, the distal shaft segment 16 may have a diameter or average transverse axial dimension in the range of about 0.5 mm to about 1.5 mm or more, sometimes about 0.7 mm to about 1.2 mm, and other times about 0.8 mm to about 1 mm. The length of the distal shaft segment 16 may be in the range of about 30 mm to about 1 meter or more, sometimes about 200 mm to about 600 mm, and other times about 300 mm to about 500 mm. The proximal housing 4 and/or the handle 18 may comprise molding, gripping materials and/or surface texturing to augment the gripping characteristics of the scope 2. For example, in FIG. 1A, the optional handle 18 comprises a knurled surface 20.

The flexibility or rigidity of the various segments of the shaft assembly 12 may vary or may be uniform. For example, the proximal shaft segment 14 and the handle 18 in FIGS. 1A and 1B may be rigid and comprise a material such as stainless steel, while the distal shaft segment 16 may comprise a flexible material such as polyimide. In examples where the shaft assembly has a flexible distal region, the scope may be inserted into steerable or other bendable instruments to permit visualization along a non-linear axis. In some embodiments, the proximal housing or the shaft assembly may comprise one or more connectors or interfaces to couple the scope to other instruments such as a multi-lumen cannula. These interfaces may include any of a variety of threaded interfaces or releasable lock interfaces, for example. The shaft assembly 12 comprises at least one visualization optic fiber, if not multiple optic fibers, to transmit the optical information from the distal end 6 of the scope 2 to the proximal housing 4, and may optionally comprise one or more illumination fibers to transmit light to the distal end 6. In other embodiments, an illumination source may be provided at the distal end, with electrical lines or traces provided to power the illumination source. The distal shaft segment 16 may also optionally comprise one or more lenses which may be use to focus the images and/or the illumination. The particular arrangement of the visualization fibers, the optional illumination fibers and the optional lenses may vary, and may affect the viewing angle 22 of the scope 2. In some embodiments, the viewing angle of the scope may be in the range of about 10 degrees to about 180 degrees, or about 45 degrees to about 135 degrees, and other times about 90 degrees to about 120 degrees. Although the viewing angle 20 schematically depicted in FIG. 1A is depicted as symmetrically aligned with respect to the longitudinal axis of the scope 2, in other examples, the viewing angle may be offset from the longitudinal axis of the distal shaft segment 16.

Other scopes that may be used are disclosed in U.S. Pat. Nos. 4,807,597 and 4,899,732, which are hereby incorporated by reference in their entirety, as well as various scopes made by Vision-Sciences (Rangeburg, N.Y.). In other embodiments, the visualization instrument may comprise a different local visualization system, such as an ultrasound imaging device that is insertable into the body using a minimally invasive procedure, such as the intravascular ultrasound systems used to visualize vascular plaques and biliary trees, for example.

Figure 2B:
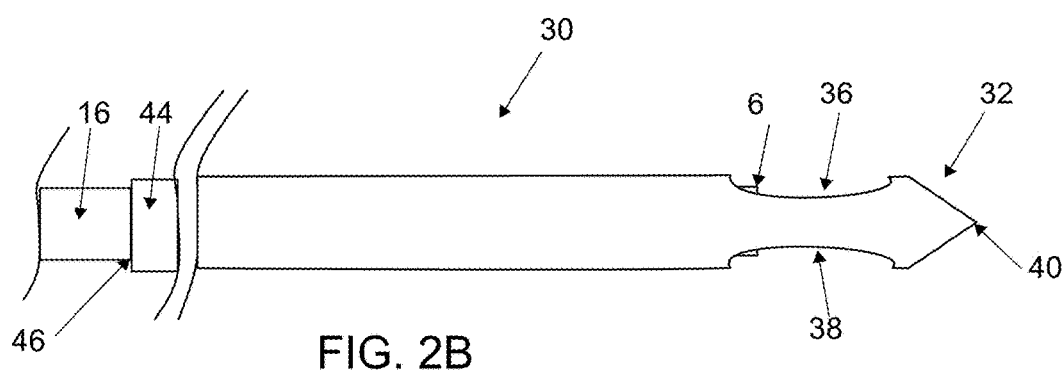
Figure 2C:
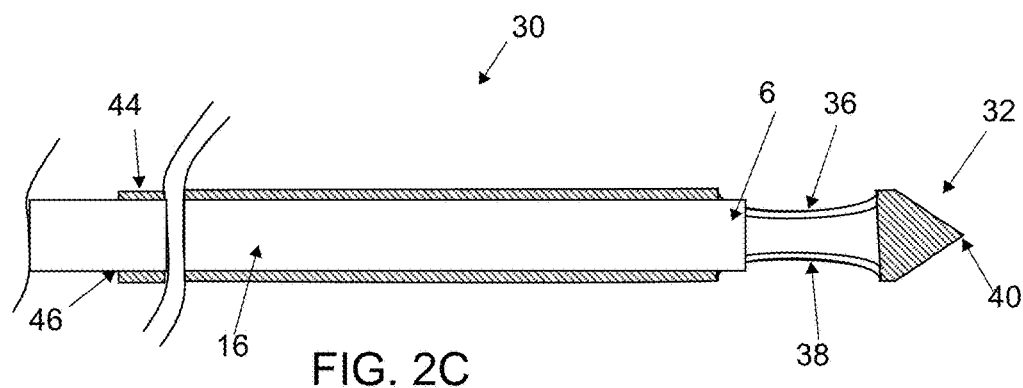
FIG. 2C is a cut-away view of the tubular penetrating member in FIG. 2B.

The scope 2 in FIGS. 1A and 1B may be inserted into an access system which is configured with one or more regions that permits viewing of the surroundings about the cutting or piercing structure used to form the access pathway. In FIGS. 2A to 2C, for example, the access system may comprise a tubular penetrating member 30 with a distal piercing tip 32 and at least one inner lumen 34 configured to receive the scope 2. In some alternate embodiments, one or more subcomponents of the scope may be integrated into the tubular penetrating member or provided in a separate device to be inserted into a different lumen. For example, in some embodiments, the scope may lack the illumination fibers, which may be provided instead in the tubular penetrating member along with an illumination connector. In this particular example, providing illumination from a different location than the distal end scope may improve the viewing of the tissue surrounding the distal piercing tip or other regions of the tubular penetrating member. In some further embodiments, the tubular penetrating member and the scope may also be integrally formed. In still other embodiments, the scope and/or tubular penetrating member may comprise one or more additional lumens which may be used, for example, for irrigation, therapy, dye or imaging agent delivery, or guidewire insertion.

The inner lumen 34 of the tubular penetrating member 30 may comprise one or more side openings 36 and 38 to permit visualization of the surroundings from the lumen 34. In this particular example, the side openings 36 and 38 are uncovered, but in other embodiments disclosed herein, one or more openings may be covered with a transparent material. As shown in FIGS. 2B and 2C, the inner lumen 34 and the side openings 36 and 38 may be configured so that the distal segment 16 and/or the distal end 6 of the scope 2 may protrude from at least one of the side openings 36 and 38. In this particular embodiment, the side openings 36 and 38 have oval configurations that are oriented along their longer dimensions with the longitudinal axis of the tubular penetrating member 30. The side openings may have a longitudinal length that may be in the range of about 0.4 mm to about 10 mm or more, sometimes about 0.6 mm to about 3 mm, and other times about 0.8 mm to about 2 mm. The openings 36 and 38 may have a width of about 0.4 mm to about 1.5 mm or more, sometimes about 0.6 mm to about 1.2 mm, and other times about 0.7 mm to about 0.9 mm. Although the side openings 36 and 38 are depicted as symmetrically spaced about 180 degrees apart along the circumference of the tubular penetrating member 30, and are longitudinally aligned, the openings may also be asymmetrically spaced around the circumference and a number of openings may be provided along the longitudinal length in or out of alignment. The distance between the most distal side openings and the distal point 40 of the piercing tip 32 may be in the range of about 0.5 mm to about 20 mm or more, sometimes about 0.8 mm to about 5 mm, and other times about 0.8 mm to about 2 mm.

Referring to FIG. 2C, although the proximal section 44 of the tubular penetrating member 30 comprises only the proximal opening 46 of the inner lumen 34, in other embodiments the proximal section may optionally comprise a handle, a housing or some other configuration. In some specific examples, the proximal opening of the inner lumen may have a flared configuration to facilitate the insertion of the scope 2 into the tubular penetrating member. In other embodiments, however, the scope may be inserted into the tubular penetrating member during manufacturing and configurations to facilitate insertion are not provided.

Figure 3:
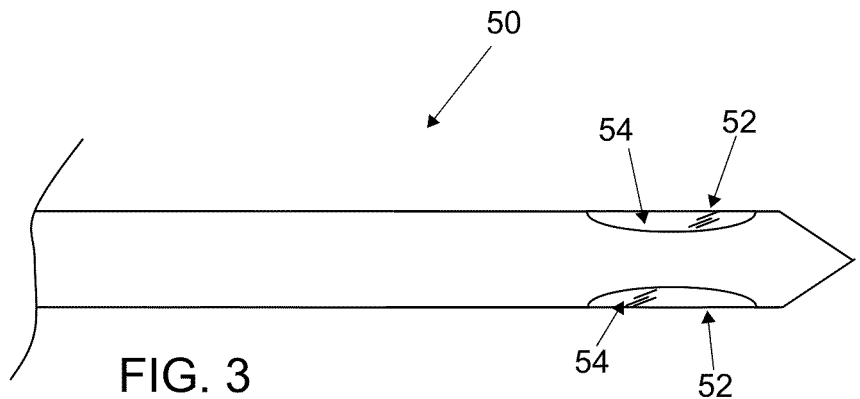
FIGS. 3 to 5 depict various other embodiments of tubular penetrating members.

As mentioned previously, in some embodiments, the side openings may be covered with a transparent material. In FIG. 3, for example, the tubular penetrating member 50 has openings 52 that are covered by transparent windows 54. The transparent window material may be an optically transparent material, including various forms of glass, nylon, Pebax, PET, FEP, PTFE, polyolefin, acrylic, polycarbonate or polyethylene, for example. In other embodiments where the visualization instrument is a non-optical device (e.g. ultrasound), the transparent window may transparent to the particular imaging modality but not to others.

Although the distal piercing tip 32 depicted in FIGS. 2A to 2C has a conical configuration and a distal point 40 that is centrally located, in other examples, the distal piercing tip may have an eccentrically located distal point, multiple distal points, or a non-conical configuration. The distal point 40 may be sharp or may be blunt. Also, the angle 42 of the distal piercing tip 32 may be different, and may be in the range of about 10 degrees to about 175 degrees, sometimes about 35 degrees to about 120 degrees, and other times about 45 degrees to about 90 degrees, for example.

Figure 4:
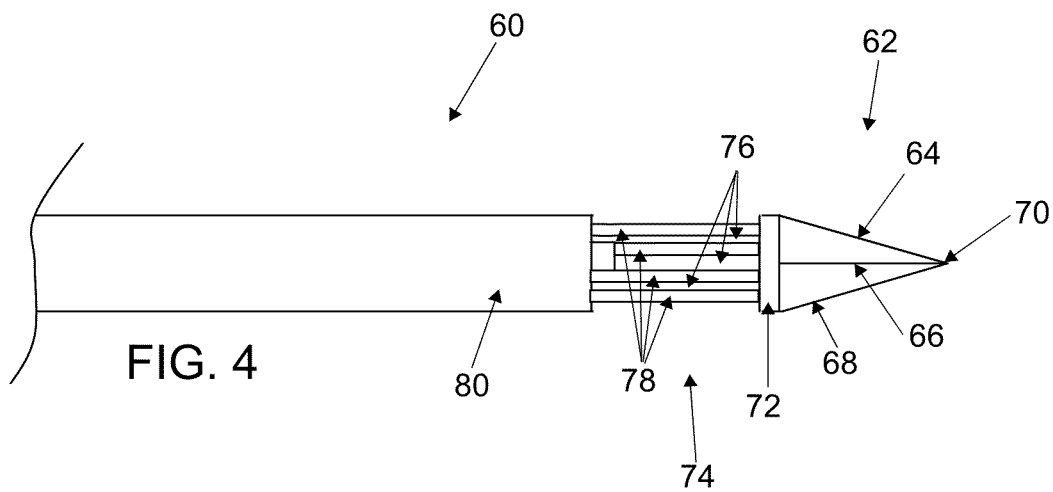
Figure 5:
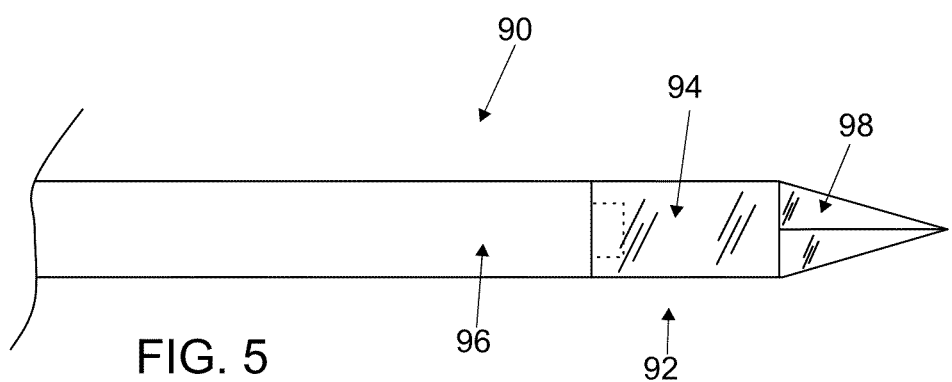

In FIG. 4, for example, the tubular penetrating member 60 comprises a distal piercing tip 62 that has a pyramidal configuration with one or more edges 64, 66 and 68. In this example, the edges 64, 66 and 68 are linear and span the distance from the distal point 70 to the base 72 of the distal piercing tip 62. The each of the edges 64, 66 and 68 may be sharp or blunt. In other embodiments, the edges may be span less than the full length of the distal piercing tip, and may have a non-linear configuration. Some non-linear configurations may include helical configurations, angular configurations, and concentric configurations, for example. As further shown in FIG. 4, the tubular penetrating member 60 comprises a distal viewing region 74 a number of rectangular openings 76 separated by struts 78 which connect the distal shaft segment 80 with the distal piercing tip 62. FIG. 5 depicts another example of a tubular piercing member 90 wherein the viewing region 92 comprises a transparent tube 94 or cylinder connecting the distal shaft segment 96 with the distal piercing tip 98. Also, the distal piercing tip 98 also comprises a transparent material.

Figure 6A:
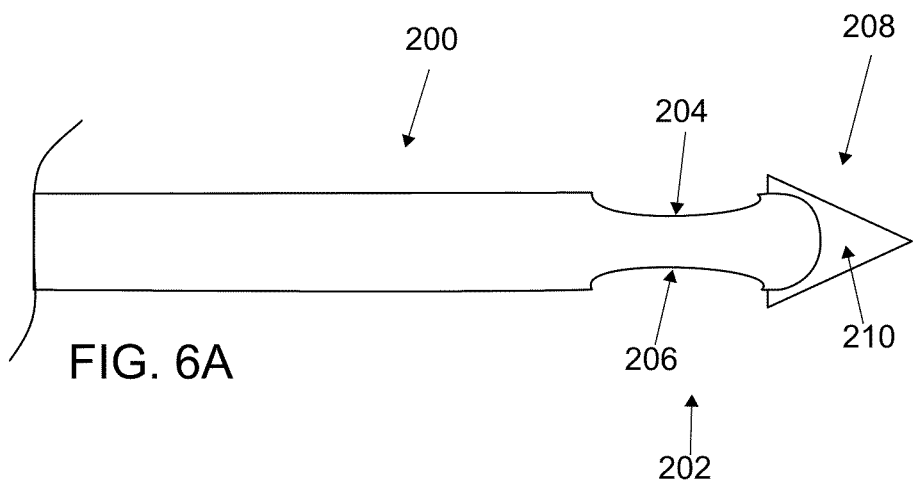
FIGS. 6A and 6B are side and superior elevational views of a tubular penetrating member comprising a blade.
Figure 6B:
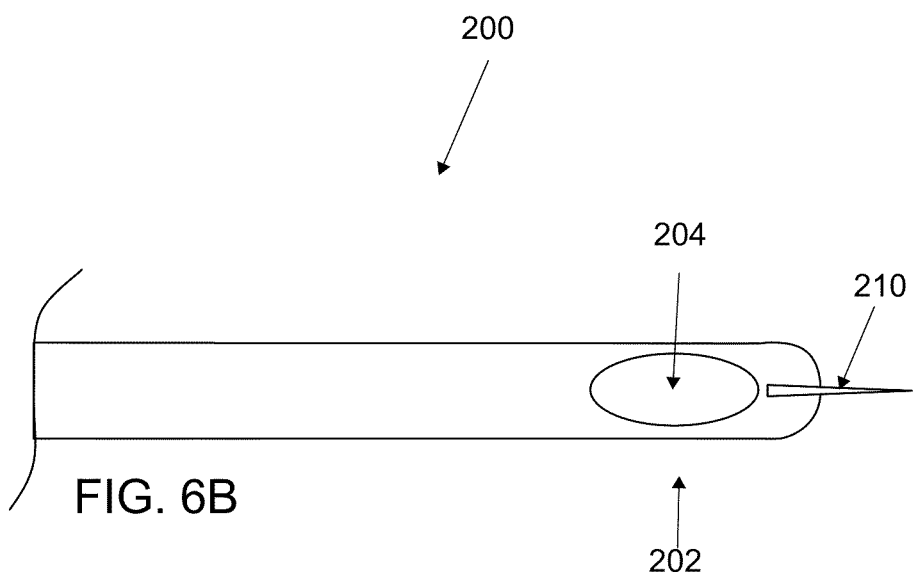

FIGS. 6A and 6B depict another embodiment of a tubular penetrating member 200, comprising a distal viewing region 202 with one or more side openings 204 and 206, along with a distal piercing tip 208 with a protruding blade 210 or other piercing configuration. Although a single blade is illustrated in FIGS. 6A and 6B, in other examples, multiple blades may be provided. Also, the blade 210 may have a triangular configuration as depicted, but may have other configurations, such as a spade configuration, a square or rounded spatula configuration, or any of a variety of other blade configurations. The blade orientation relative to the distal viewing region or the openings may also vary. In FIGS. 6A and 6B, for example, the single blade 210 is located in a plane that lies symmetrically in the middle of each opening 204 and 206, but in other embodiments, the blade may be located in a plane that lies symmetrically between the openings, or a plane that is offset or angled with respect to the central longitudinal axis of the tubular penetrating member.

Figure 7A:
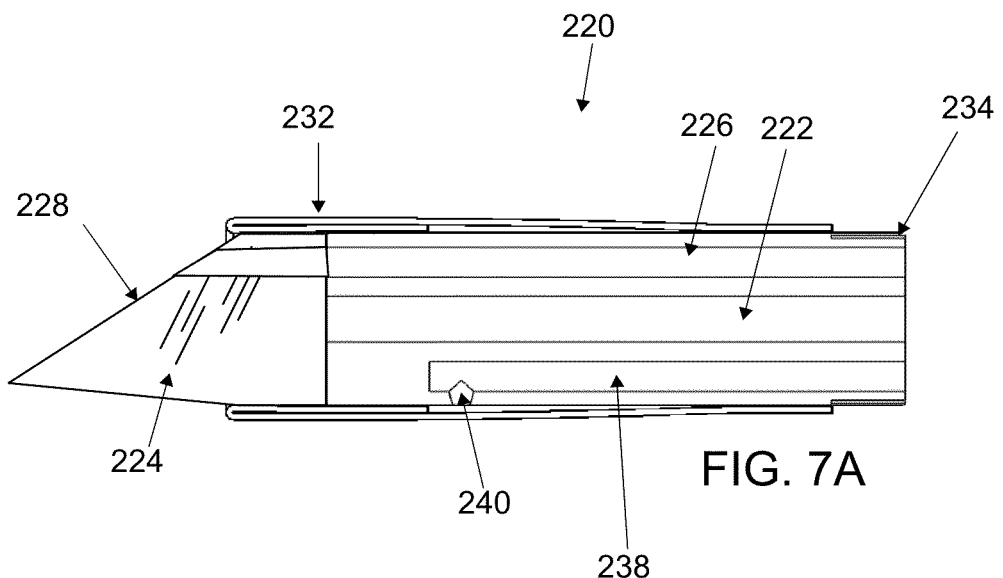
FIGS. 7A and 7B are longitudinal cross-sectional views of a multi-lumen penetrating member with an optional balloon in the deflated and inflated states, respectively.
Figure 7B:
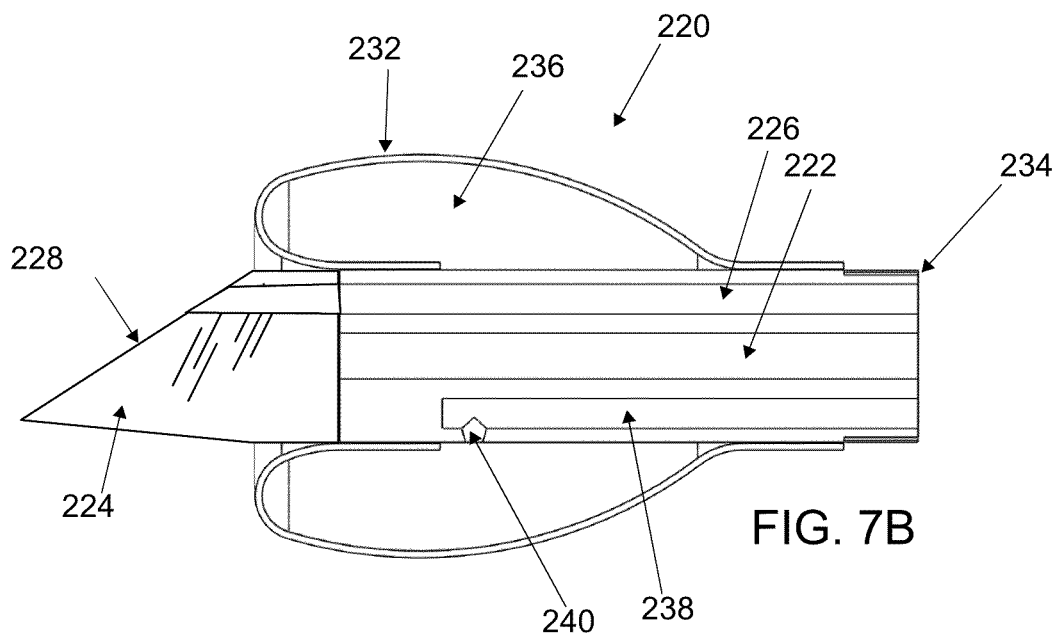

As mentioned previously, some embodiments of the penetrating member may comprise a multi-lumen configuration. In FIGS. 7A and 7B, for example, the penetrating member 220 comprises a scope lumen 222 for the insertion of a fiberoptic scope. The scope lumen 222 may be used to provide visualization through the transparent piercing tip 224 of the penetrating member 220. The penetrating member may also comprise an accessory lumen 226 that may be used for any of a variety of functions. In the particular configuration in FIGS. 7A and 7B, the accessory lumen 226 has a distal lumen 230 that continues through the transparent piercing tip 224. The transparent piecing tip 224 in this example comprises a beveled configuration that provides a large planar surface 228. In some instances, the large planar surface 228 may improve the viewing through transparent materials compared to multiple smaller angled surfaces. Although the scope lumen 222 has a generally linear configuration which is not at a perpendicular angle to the large planar surface 228, in some embodiments the scope lumen may be angled closer to a perpendicular angle to the large planar surface 228, or any other viewing surface.

The penetrating member 220 in FIGS. 7A and 7B further comprises an optional balloon 232. The balloon 232 may be bonded to the shaft 234 of the penetrating member 220 to form a balloon cavity 236 which may be inflated by an inflation lumen 238 of the shaft 234 at an inflation opening 240. The balloon 232 may be inflated with a gas or a liquid, such as saline. In some instances, the balloon 232 may be used during an access procedure to enlarge the access pathway to push away the tissue surrounding the penetrating member 220, which may improve the visualization and identification of the tissue, and may also dilate the pathway to permit passage of larger instruments.

The balloon 232 may comprise any of a variety of stretchable and non-stretchable medical balloon materials, including but not limited to polyurethane or PET, for example. The balloon assembly 230 may have any of a variety of shapes upon inflation, including but not limited to a cylindrical, conical, spherical, elliptical, tapered or stepped configuration for example. The balloon 232 in FIG. 7B has an inflated toroidal shape that is symmetrically arranged about the circumference of the shaft 234, but in other embodiments, the balloon shape may be offset of eccentrically arranged with respect to the shaft. In the uninflated state, the balloon 232 may have an outer diameter of about 4 mm or less, sometimes about 3.6 mm or less, and other times about 3 mm or less. In the inflated state, the balloon 232 may have a maximum outer diameter of about 4 mm or more, sometimes about 5 mm or more, and other times about 6 mm or more. The longitudinal length of the balloon 232, as mounted on the shaft 234, may be in the range of about 3 mm to about 20 mm, sometimes about 4 mm to about 10 mm, and other times about 5 mm to about 8 mm, for example.

The balloon 232 may be attached to the shaft 234 by adhesives or by heat bonding, for example. In some embodiments, attachment structures or processes may be used, which improve the sealing between the balloon and the tubular shaft to support the use of higher inflation pressures without separating the balloon from the tubular shaft. For example, crimp rings or heat shrink tubing may be used to augment the bonding or attachment process. The crimp rings or shrink tubing may be applied temporarily to facilitate setting of other bonding processes. In other embodiments, the crimp rings or shrink tubing may be incorporated into the final assembled product.

Figure 8:
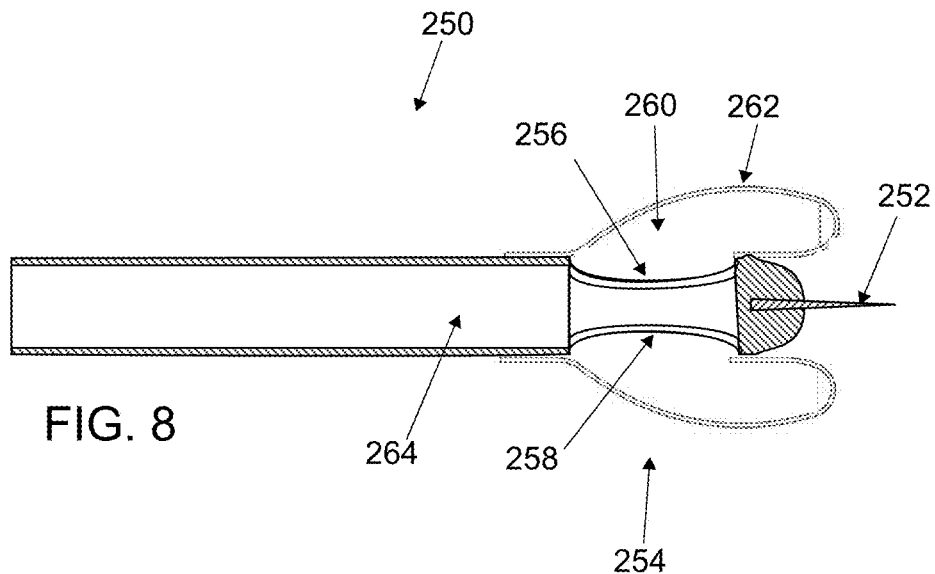
FIG. 8 is a longitudinal cross-sectional view of a penetrating member with a transparent viewing balloon.
Figure 9:
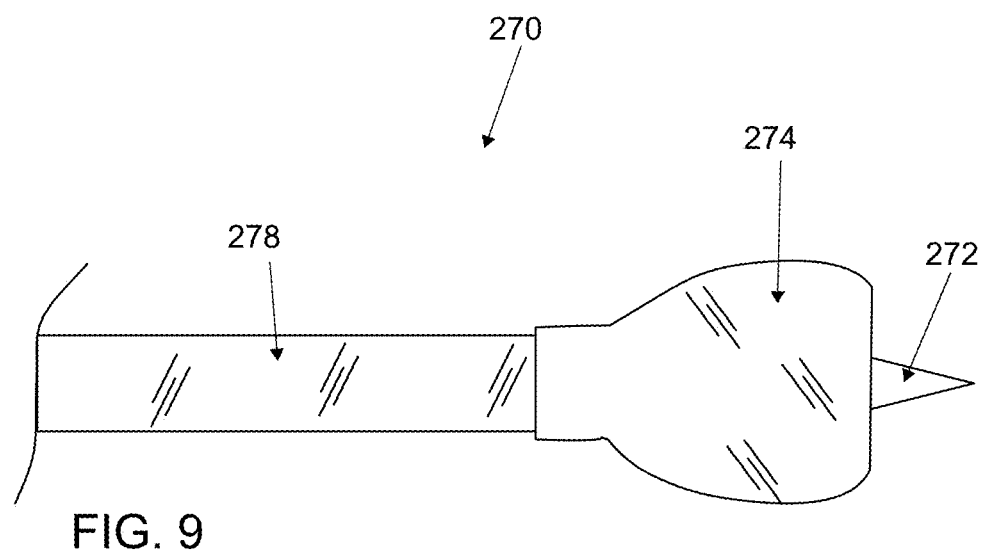
FIG. 9 is a side elevational view of a penetrating member with a transparent viewing balloon and a transparent shaft segment.

In some embodiments, the side openings of the penetrating member may be configured so that the visualization occurs through the balloon and the balloon cavity. This may permit the user to selectively adjust the distance of any abutting tissue by selectively inflating or deflating the balloon. In FIG. 8, for example, the penetrating member 250 comprises a distal blade 252 and a viewing region 254 with two side openings 256 and 258. The side openings 256 and 258 are in communication with the balloon cavity 260 of a balloon 262 that sealed around the openings 256 and 258. Here the inner lumen 264 of the penetrating member 250 is configured to receive a scope, but to also inflate and deflate the balloon cavity 260. The scope used with this particular penetrating member 250 may be configured to withstand the pressure to which the balloon 262 may be inflated. FIG. 9 depicts another embodiment of a penetrating member 270, comprising a conical penetrating tip 272, a transparent inflatable balloon 274 and a transparent shaft 276. In some instances, a transparent shaft may permit the visualization of the tissues and structures along the entire access pathway, not just the region surrounding the distal end of the penetrating member 270.

Figure 10A:
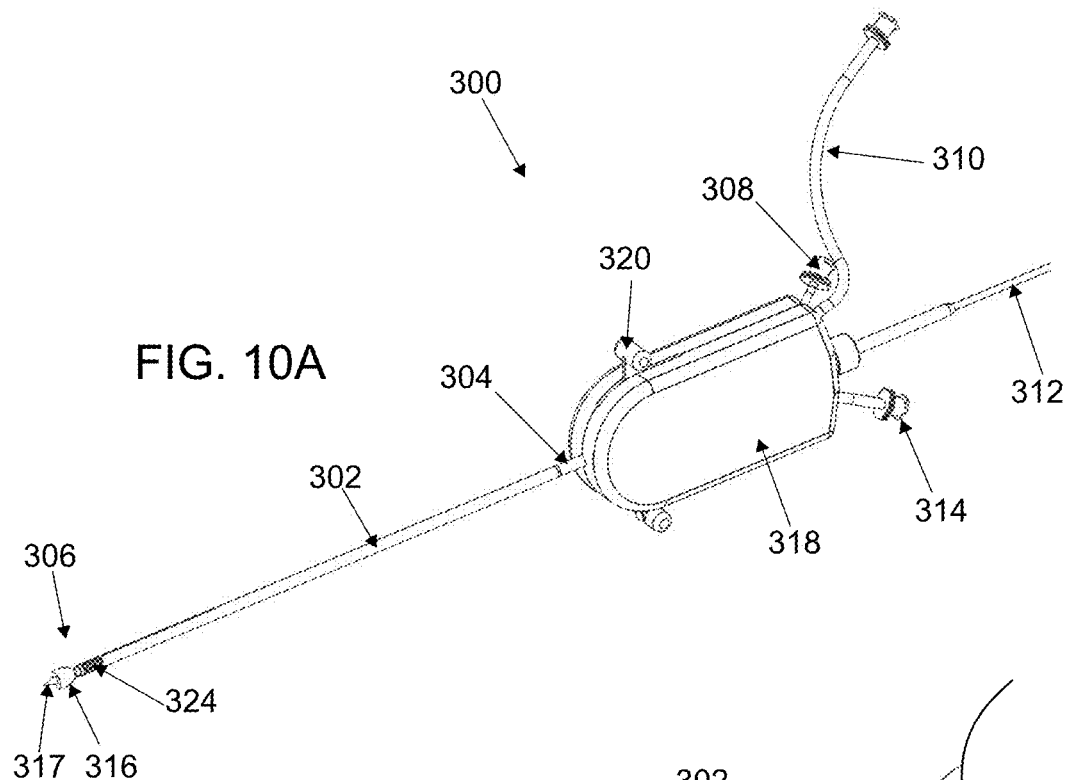
FIG. 10A is a perspective view of a penetrating member with a balloon.
Figure 10B:
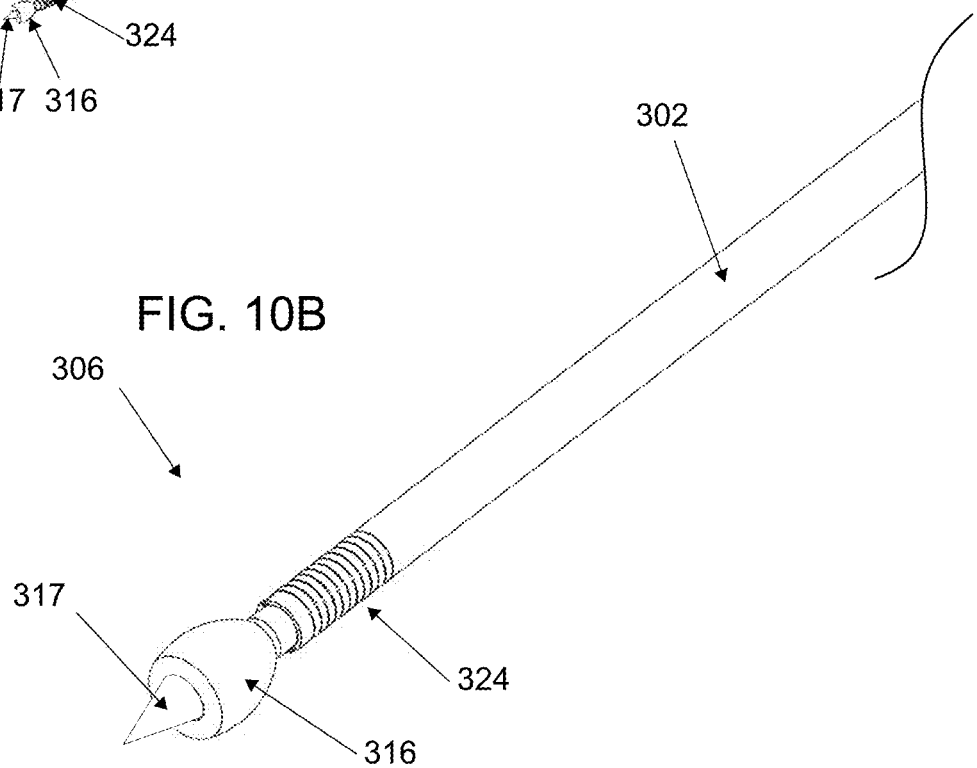
FIG. 10B is a detailed view of the distal end of the penetrating member in FIG. 10A.

FIGS. 10A and 10B are general and detailed views of one embodiment of a balloon penetrating member 300, comprising a tubular shaft 302 with a proximal end 304 and a distal end 306. The proximal end 304 of the penetrating member 300 is attached to an optional housing 318, while the distal end 306 comprises an inflatable balloon 316 and a penetrating tip 317. Various ports 308, 310, 312, and 314 may be optionally provided on the shaft or the optional housing 318, and may be configured for any of a variety of usages, including but not limited to infusion/drainage/suction of fluids or materials, insertion/removal or supporting an endoscope or fiber-optic device, inflation/deflation of the inflatable balloon 316, and for insertion/removal or support of other instruments or tools. The housing 318 may also an optional steering mechanism 320.

The steering mechanism 320 may be configured to cause bending of the shaft 302 at one or more bending regions 324. In FIG. 10C, the steering mechanism 320 is depicted with the port tubing and a portion of the housing 318 removed. The steering mechanism 320 comprises a lever 322 that is configured to rotate or pivot at a lever axle 390. In other embodiments, the steering mechanism 320 may comprise a slide, knob or other configuration. The lever 322 is attached to two control members 392 that are slidable located along the length of the shaft 302 and are attached at a distal location of the shaft 302. The movement range and force may be augmented by one or more bias members 398 acting upon the lever 322. The bias members 198 may comprise helical springs as depicted in FIG. 10C, but may also comprise leaf springs or any other type of bias member configuration. The movement range of the lever 322 may also be affected by the size and/or configuration of the lever openings 399 provided in the housing 318. In some embodiments, an optional locking mechanism may be provided to substantially maintain the lever in one or more positions.

The control members 392 may comprise wires, threads, ribbons or other elongate structures. The flexibility and/or stiffness of the control member 392 may vary depending upon the particular steering mechanism. In further embodiments, the characteristics of the control member 392 may also vary along its length. In embodiments comprising two or more control members, the control members need not be configured symmetrically, e.g. having the same length, cross-sectional area or shape, or opposite attachment sites with respect to the longitudinal axis of the tubular shaft.

Also, individual control members need not have the same configuration along their lengths.

The bending range of bending regions 324 may vary. The balloon penetrating member 300 may be configured with a one-sided or a two-sided bending range with respect to the neutral position of the shaft. The bending range may be in the range of about 0 degrees to about 135 degrees, sometimes from about 0 degrees to about 90 degrees, and other times about 0 degrees to about 45 degrees, and still other times about 0 degrees to about 15 or about 20 degrees. The bending range of the other side, if any, may be less than, equal to, or greater than the first side.

As mentioned previously, a penetrating member with direct visualization capabilities may be used for a variety of medical procedures in a variety of fields. A penetrating member with a scope may be used to provide the initial access to a particular target site that would otherwise be performed blindly, under fluoroscopy, or using external imaging modalities. In one particular example, a penetrating member may be used to provide access to the epidural or paravertebral region of the cervical, thoracic or lumbar spine. One access to the region is achieved, endoscopic instruments may be positioned using the access pathway to accomplish a variety of spinal procedures, including lysis of adhesions, anesthetic injections, nucleotomy, discectomy and foraminotomy, and laminectomy, for example. Some examples are described below.

Figure 11:
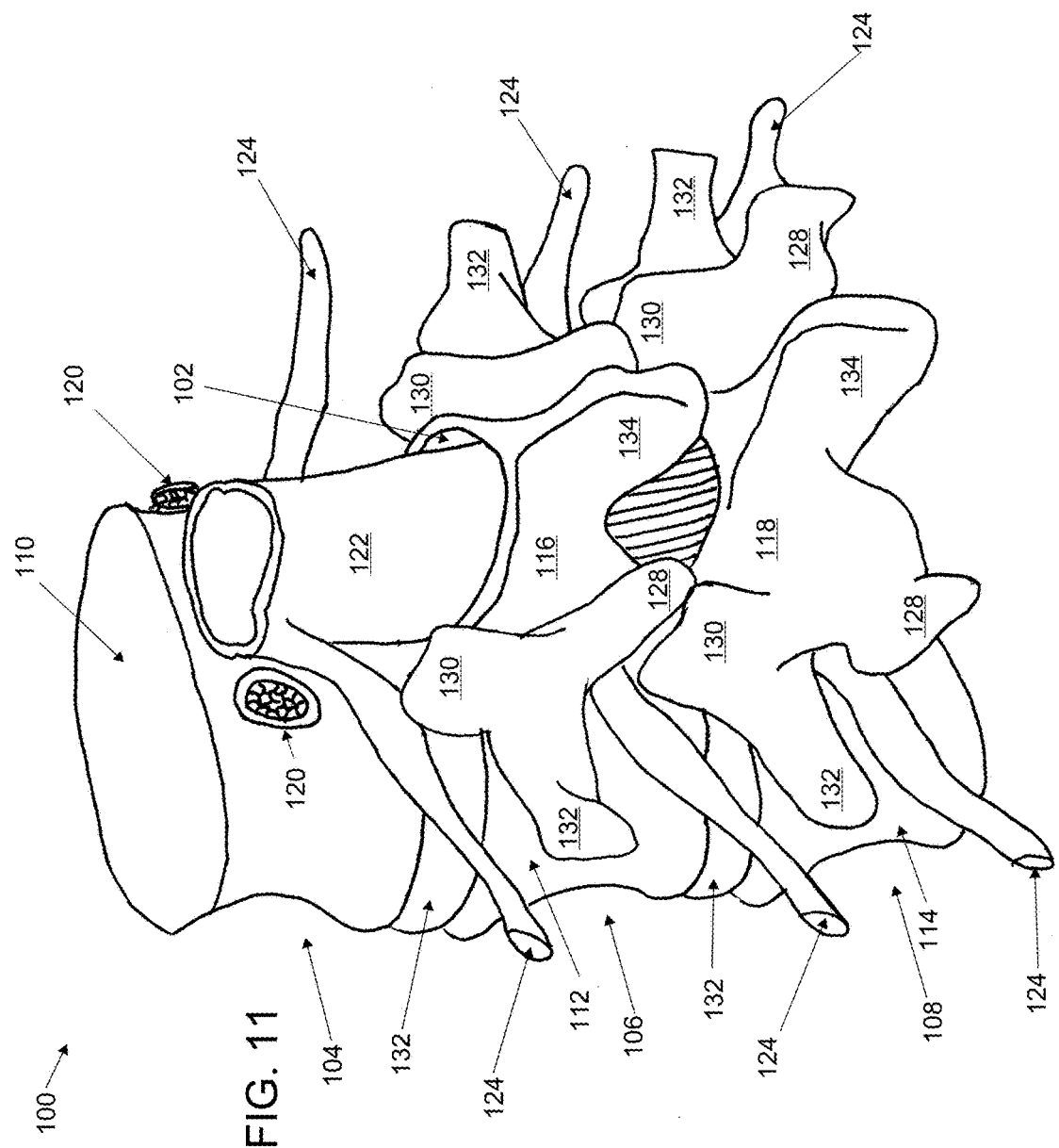
FIG. 11 is a schematic perspective view of a portion of lumbar vertebrae.
Figure 12:
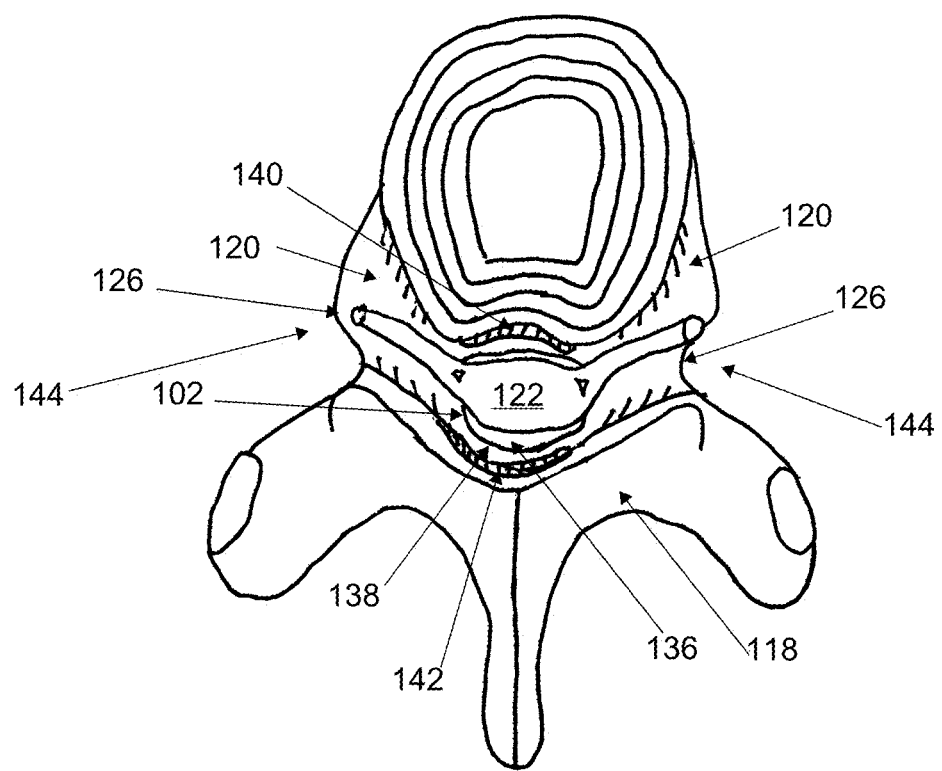
FIG. 12 is a schematic superior elevational view of a lumbar vertebra.
Figure 13:
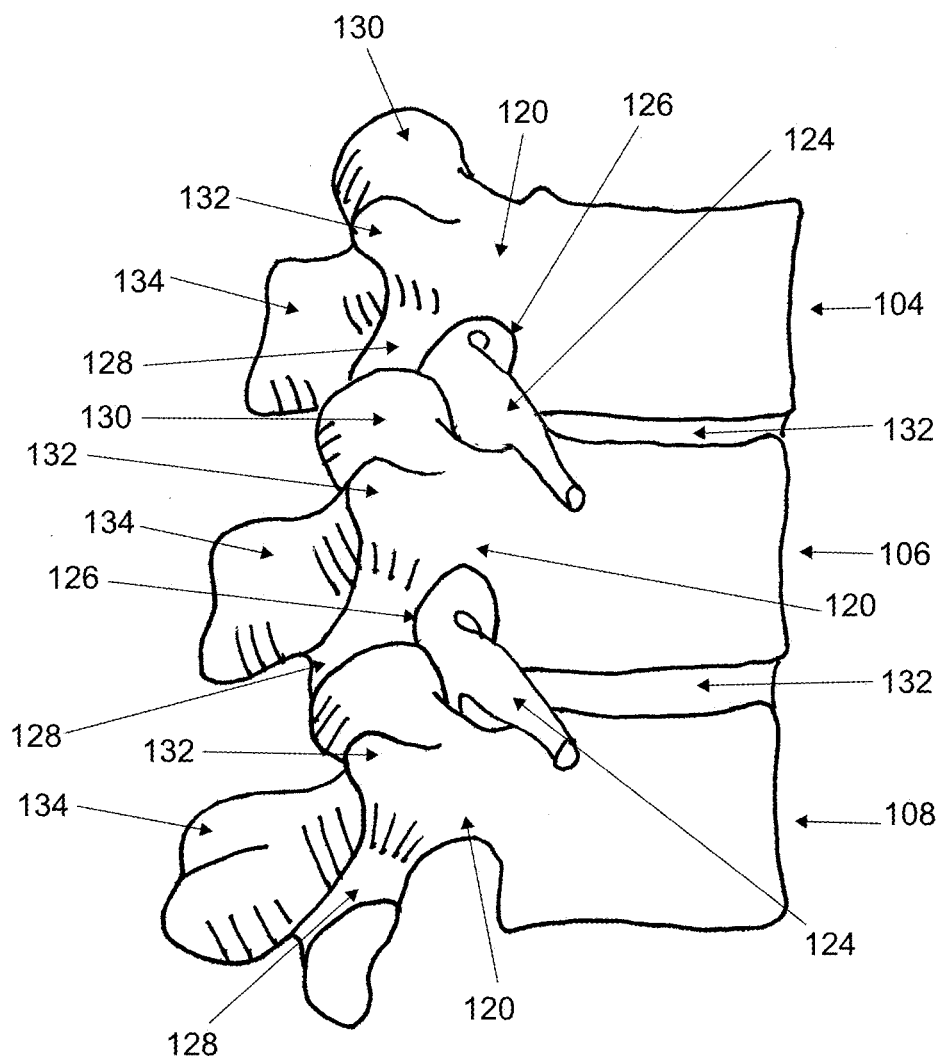
FIG. 13 is a schematic side elevational view of lumbar vertebrae.

FIGS. 11 to 13 are schematic views of a lumbar region of a spine 100. The vertebral canal 102 is formed by a plurality of vertebrae 104, 106, and 108, which comprise vertebral bodies 110, 112 and 114 anteriorly and vertebral arches 116 and 118 posteriorly. The vertebral arch and adjacent connective tissue of the superior vertebra 104 has been omitted in FIG. 11 to better illustrate the spinal cord 122 within the vertebral canal 102. Spinal nerves 124 branch from the spinal cord 122 bilaterally and exit the vertebral canal 102 through intervertebral foramina 126 (seen best in FIGS. 12 and 13) that are formed by the adjacent vertebra 104, 106 and 108. The intervertebral foramina 126 are typically bordered by the inferior surface of the pedicles 120, a portion of the vertebral bodies 104, 106 and 108, the inferior articular processes 128, and the superior articular processes 130 of the adjacent vertebrae. Also projecting from the vertebral arches 116 and 118 are the transverse processes 132 and the posterior spinous processes 134 of the vertebrae 106 and 108. Located between the vertebral bodies 110, 112 and 114 are the vertebral discs 132.

Referring to FIG. 12, the spinal cord 122 is covered by a thecal sac 136. The space between the thecal sac 136 and the borders of the vertebral canal 102 is known as the epidural space 138. The epidural space 138 is bound anteriorly and posteriorly by the longitudinal ligament 140 and the ligamentum flavum 142 of the vertebral canal 102, respectively, and laterally by the pedicles 120 of the vertebral arches 116 and 118 and the intervertebral foramina 126. The epidural space 138 is contiguous with the paravertebral space 144 via the intervertebral foramina 126.

Figure 14A:
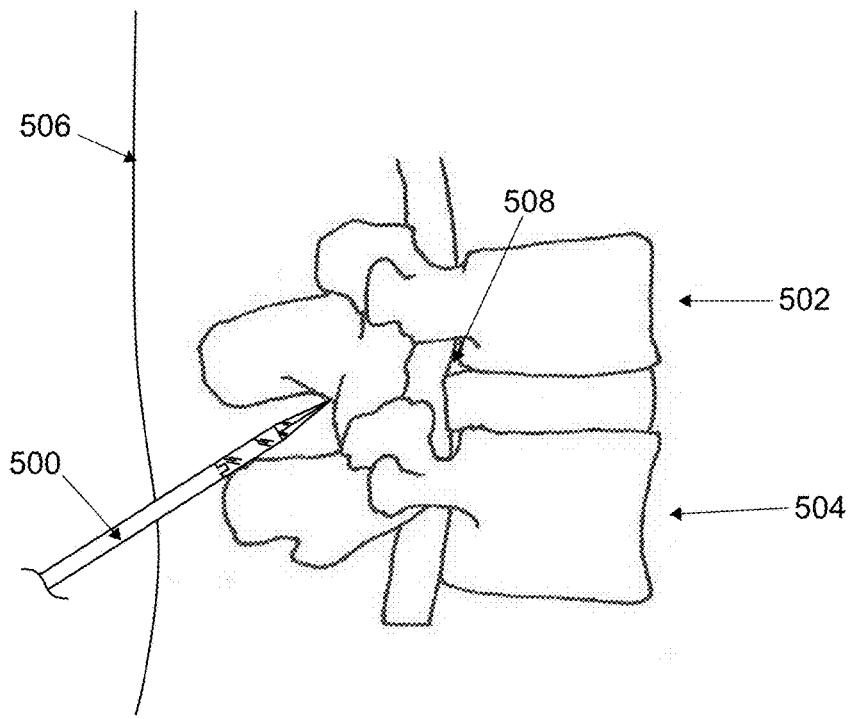
FIGS. 14A and 14B are schematic side and superior elevational views of a caudal spinal access procedure.
Figure 14B:
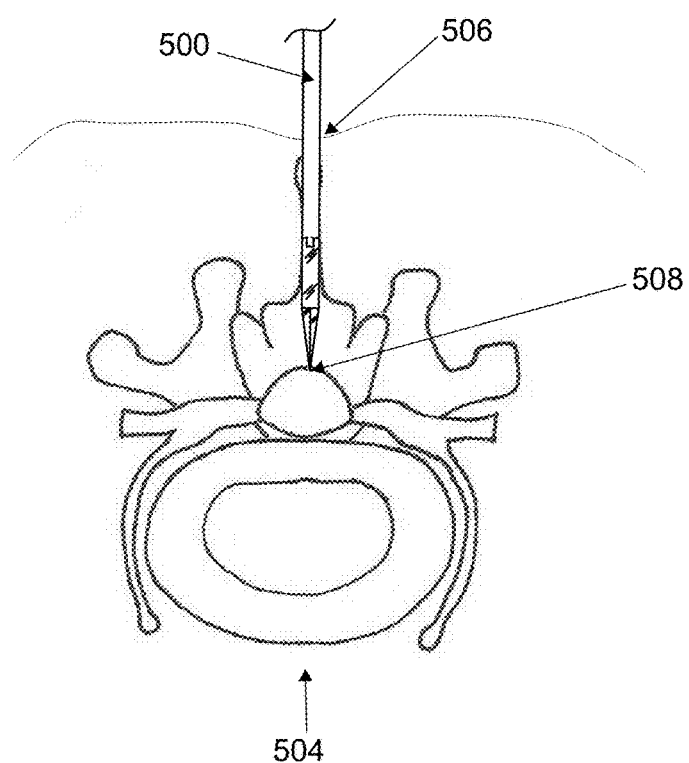

With this anatomical framework, a number of exemplary access procedures may be performed. The particular access procedure may depend on the suspected diagnosis and/or the likely treatment to be performed. For example, FIGS. 14A and 14B schematically depict a midline spinal access procedure using a penetrating member 500 that forms an access pathway between two adjacent vertebrae 502 and 504, which may be used to access the central spinal canal and epidural space of a patient. Such procedures have been used, for example, to provide epidural anesthesia but, intravascular injection of the anesthesia or other injuries have occurred due to inaccurate needle placement.

To perform an epidural access procedure using a penetrating member with a direct visualization feature, the patient may be placed in a sitting or lateral decubitus position with the spine arched anteriorly. The target level along the spine is identified using surface landmarks or other indicia and the skin is prepped and draped. Local anesthesia is achieved in the skin region. The penetrating member 500 with a scope is inserted into the skin tissue 506 until the ligamentous tissue of the interspinous ligament is visualized and monitored until the tip of the penetrating member 500 passes out of the anterior surface of the ligament and into the epidural space 508 In some embodiments, the scope may be removed from the penetrating member 500 while holding the penetrating member 500 in position, and a guidewire may be inserted through the penetrating member and into the epidural space. The penetrating member 500 may then be removed and a dilator may be optionally inserted and withdrawn over the guidewire. An introducer is then optionally placed over the guidewire and the guidewire is then optionally removed. An endoscope or other tubular instrument with a miniscope or fiberscope is then inserted through the introducer and/or over the guidewire to revisualize the epidural space. In some instances, the miniscope or fiberscope withdrawn from the penetrating member may be inserted into the endoscope and tubular instrument to provide visualization.

Figure 15A:
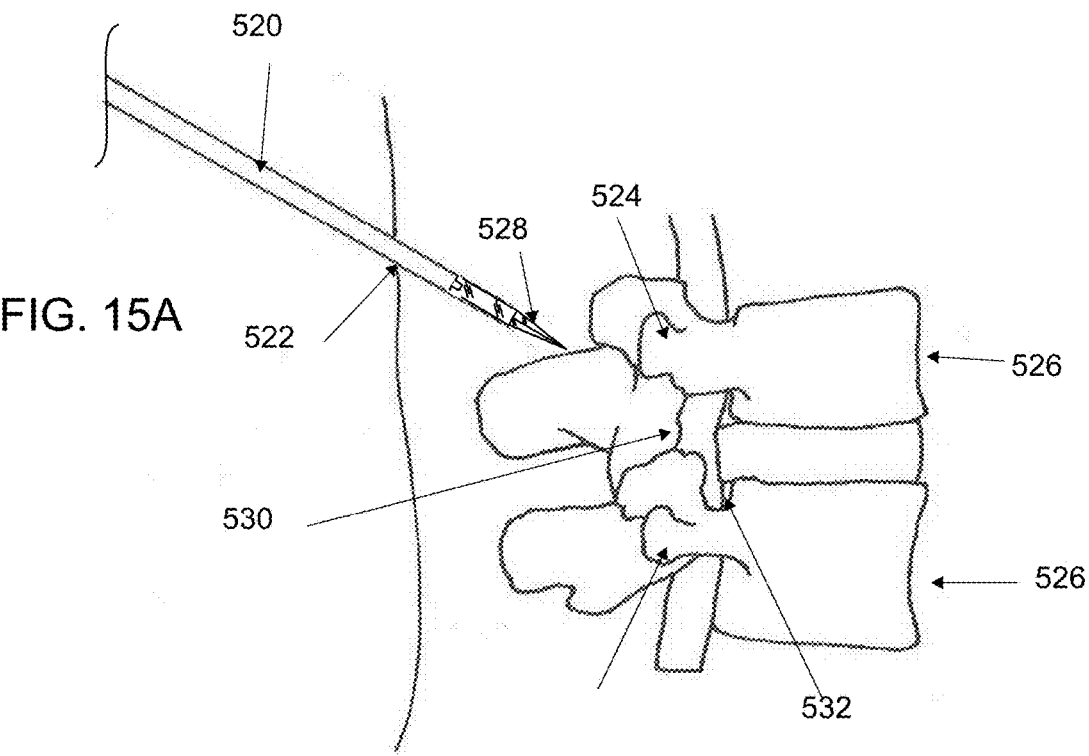
FIGS. 15A and 15B are schematic side and superior elevational views of a postero-lateral spinal access procedure.
Figure 15B:
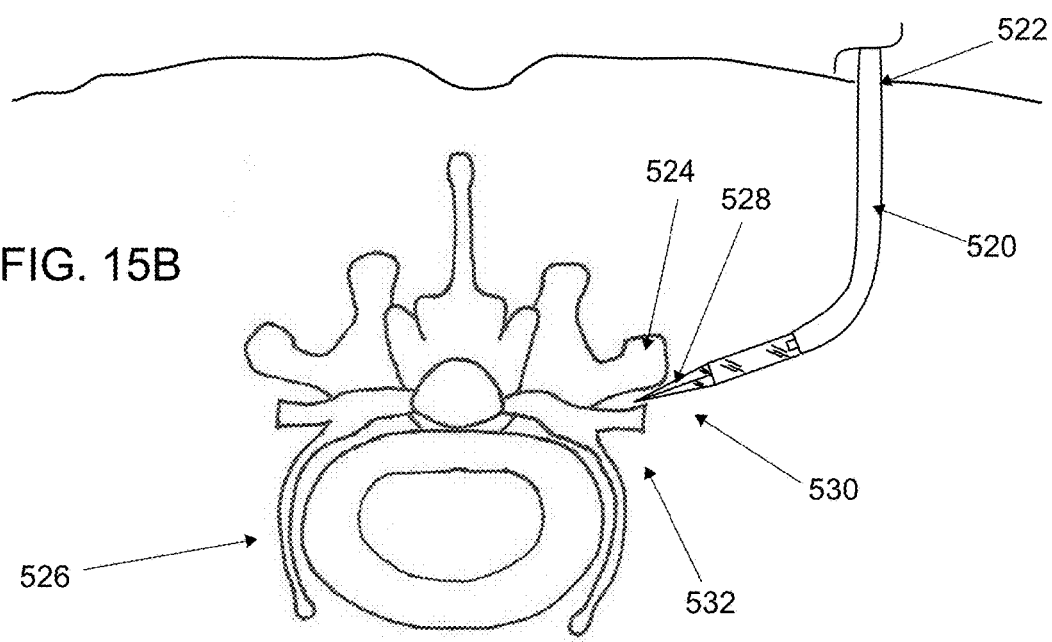

In another procedure, access to an intervertebral foramen is achieved using a penetrating member with direct visualization. In this procedure, the patient is placed in a prone position. The target site is identified and the skin is prepped and draped. Referring to FIGS. 15A and 15B, Anesthesia is achieved and a penetrating member 520 with a scope is inserted into the skin tissue 522 at a location about 10 cm from the midline. The penetrating member 520 may be angled at the skin tissue 522 to about a 35 degree angle to the midsaggital plane, or may be steered midline after at least partially penetrating the skin tissue 522. After partial penetration of the skin tissue, the penetrating member 520 s steered toward the midline to avoid interference from the spinous processes 524 of the vertebrae 526 and/or to achieve a particular access angle upon reaching the target site. The tissue around the piercing tip 528 of the penetrating member 520 is visualized as the penetrating tip 524 is piercing intact body tissue, watching for the penetrating tip 524 to emerge from the body tissue and into the paravertebral space 530 adjacent to the foramen 532. The insertion of the penetrating member then stopped to avoid inadvertent damage to the nerves located in the intervertebral foramen and the penetrating member 520 is exchanged for other therapeutic or diagnostic instruments.

The penetrating members described herein may be used for any of a variety of access procedures. In some examples, a penetrating member may be inserted through the chest wall and visualization is used to determine when the pleural cavity filled with pleural fluid is reached, thereby reducing the risk of puncturing the lung and causing a pneumothorax. In another example, a penetrating member may be inserted through the abdominal wall and visualization is used to determine when the abdominal cavity is reached, thereby reducing the risk of perforating other abdominal organs such as the liver or the bowel.

Figure 16:
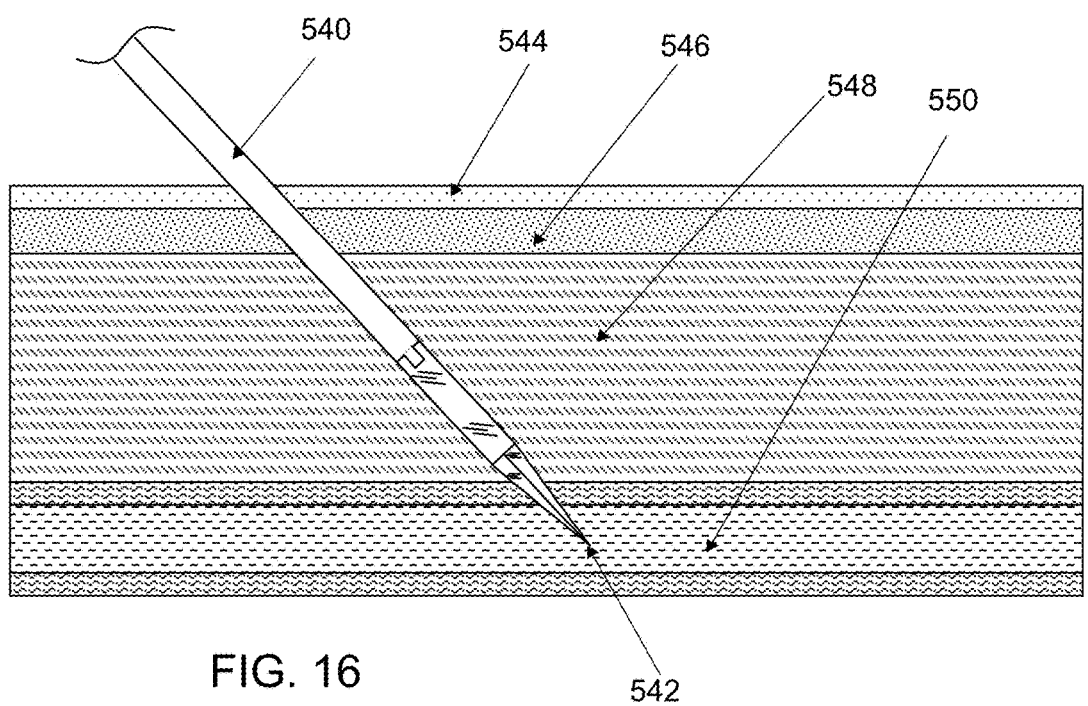
FIG. 16 is a schematic cross-sectional view of a vascular access procedure.

In addition to reducing the risk of inadvertent puncture or damage to adjacent structures, the penetrating member with direct visualization capabilities may be used to identify various body structures that may be difficult to determine by indirect or external imaging, tactile response, or other surrogate measures. For example, venous and arterial access may be challenging for a number of reasons, such as a volume-depleted patient due to blood loss or dehydration, or when access was initially achieved but further insertion of the access instrument resulted in puncture through the distal lumen surface and out of the target site, or is dissecting along a wall of the artery. In FIG. 16, for example, a penetrating member 540 with a scope is inserted into the groin region of a patient achieve femoral artery access. The piercing tip 542 of the penetrating member 540 is inserted through the skin layers 544 and 546, and then through the underlying connective tissue 548. The tissue surrounding the piercing tip 542 is visualized as the penetrating member 540 is inserted, looking for a blood flash indicative of entering the artery 550, but also checking whether the femoral vein was accessed, or whether the penetrating member 540 has passed next to any adjacent structures. When this occurs, the penetrating member 540 may be partially withdrawn and redirected toward the target site, based upon the landmarks visualized from the penetrating member 540.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. For all the embodiments described herein, the steps of the method need not be performed sequentially.

What is claimed as new and desired to be protected by Letters Patent of the United States is:

1. A system for performing an access procedure, comprising:
    a miniscope, comprising:
        a video connector located about a proximal end of the miniscope;
        a lens located about a distal end of the miniscope; and
        a flexible shaft segment including an illumination optic fiber and a viewing optic fiber; and
    an elongated piercing member, comprising:
        a shaft having a proximal end and a distal end;
        a penetrating tip interfaced to the distal end of the shaft, the penetrating tip having a proximal end and a distal end, the distal end of the penetrating tip having a distal planar surface and the proximal end of the penetrating tip having a proximal planar surface, the distal planar surface ending in a distal tip, the penetrating tip being optically transparent;
        a first lumen extending from the proximal end of the shaft to the distal end of the penetrating tip, the first lumen passing through the distal planar surface of the optically transparent penetrating tip at a location proximal to the distal tip of the distal planar surface; and
        a second lumen configured to receive the miniscope, the second lumen extending from the proximal end of the shaft to the distal end of the shaft, such that the second lumen abuts and terminates at the proximal planar surface of the penetrating tip,
        a central longitudinal axis of the second lumen being configured to extend through the proximal and distal planar surfaces of the penetrating tip.

2. The system of claim 1, wherein the miniscope is pre-inserted into the elongated piercing member.

3. The system of claim 1, wherein the penetrating tip comprises at least one cutting edge.

4. The system of claim 1, wherein the penetrating tip comprises a flat blade structure.

5. The system of claim 1, wherein the elongated piercing member further includes a third lumen.

6. The system of claim 5, wherein one or more of the first, second, and third lumens is a fluid lumen.

7. The system of claim 5, further comprising an expandable member connected to the shaft.

8. The system of claim 7, wherein the expandable member comprises a balloon member.

9. The system of claim 8, wherein the third lumen is a balloon inflation lumen.

10. The system of claim 7, wherein the expandable member includes an optically transparent material.

11. The system of claim 7, wherein the elongated piercing member further includes a viewing window.

12. The system of claim 11, wherein the viewing window includes a viewing opening.

13. The system of claim 11, wherein the viewing window includes an optically transparent material.

14. The system of claim 11, wherein the viewing window is located at the distal end of the second lumen.

15. The system of claim 1, wherein the elongate piercing member further comprises a flexible segment.

* * * * *